(12) United States Patent
Haberkorn

(10) Patent No.: US 8,303,913 B2
(45) Date of Patent: Nov. 6, 2012

(54) TISSUE PROCESSOR FOR TREATING TISSUE SAMPLES

(75) Inventor: Claus Haberkorn, Dielheim (DE)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 100 days.

(21) Appl. No.: 12/905,061

(22) Filed: Oct. 14, 2010

(65) Prior Publication Data

US 2011/0091961 A1    Apr. 21, 2011

(30) Foreign Application Priority Data

Oct. 21, 2009   (DE) .......................... 10 2009 050 048

(51) Int. Cl.
  *A61B 10/00*   (2006.01)

(52) U.S. Cl. ......... 422/536; 422/500; 422/509; 422/561

(58) Field of Classification Search .................... 422/50, 422/500–503, 509, 536, 561
See application file for complete search history.

(56) References Cited

U.S. PATENT DOCUMENTS

2005/0232074 A1* 10/2005 Higashihara et al. ......... 366/273

FOREIGN PATENT DOCUMENTS

| DE | 202004013715 U1 | 12/2004 |
| DE | 112006000814 T5 | 2/2008 |
| EP | 1186653 A2 | 3/2002 |

* cited by examiner

*Primary Examiner* — Jyoti Nagpaul
(74) *Attorney, Agent, or Firm* — Hodgson Russ LLP

(57) ABSTRACT

A tissue processor for treating tissue samples comprises a process chamber (10) in which the tissue samples can be treated with at least one liquid. The process chamber (10) is formed as a vessel of a magnetic stirrer. In the process chamber, a stirring body (16) for stirring the liquid is arranged, wherein the stirring body (16) comprises at least one magnet (40*a*, 40*b*) with the aid of which the stirring body (16) can be set in rotation by a drive unit (20) of the magnetic stirrer, and at least one vane (28*a* to 28*f*) by which the liquid to be stirred is stirred when the stirring body (16) rotates. According to a first aspect of the invention, the stirring body (16) has at least three vanes (28*a* to 28*f*), according to a second aspect of the invention, the stirring body (16) has at least one further magnet (40*b*). The north pole (46) of the one magnet (40*a*) and the south pole (50) of the further magnet (40*b*) face the drive unit (20).

10 Claims, 11 Drawing Sheets

TISSUE PROCESSOR FOR TREATING TISSUE SAMPLES

CROSS REFERENCE TO RELATED APPLICATIONS

This application claims priority of German patent application number 10 2009 050 048.0 filed Oct. 21, 2009, the entire disclosure of which is incorporated by reference herein.

FIELD OF THE INVENTION

The invention relates to a tissue processor for treating tissue samples. The tissue processor comprises a process chamber which has a bottom and in which the tissue samples can be treated with at least one liquid. Moreover, the tissue processor comprises a drive unit which is arranged on a side of the bottom facing away from the process chamber. The process chamber is formed as a vessel of a magnetic stirrer. In the process chamber, a stirring body for stirring the liquid contained in the process chamber is arranged, which stirring body can be set in rotation in a contact-free manner with the aid of the drive unit. The stirring body comprises at least one vane by which the liquid to be stirred is stirred when the stirring body is rotated.

BACKGROUND OF THE INVENTION

In particular, tissue processors serve to treat tissue samples for the preparation of the tissue samples for a later microscopic examination. For this, the tissue samples are treated with liquids in a process chamber, the so-called retort. In order to achieve a uniform treatment of the tissue samples with the liquids, it is necessary that the liquids have homogeneous properties, in particular a uniform heat distribution, in the process chamber. In order to achieve this, the process chamber is formed as a vessel of a magnetic stirrer, and a stirring body for stirring the liquid contained in the process chamber is arranged in the process chamber, which stirring body can be set in rotation with the aid of a drive unit of the magnetic stirrer. The stirring effect and thus also the time which is required to achieve the desired heat distribution is above all dependent on the design of the stirring body.

One possibility of forming the stirring body is to form the stirring body in the shape of a bar by using a coated bar magnet. In practice, such a stirring body is also referred to as stir bar. When stir bars are used, it is disadvantageous that these move in an uncontrolled manner in the process chamber, that only a low stirring effect is achieved by the stir bars, and that only small forces can be transmitted from the drive unit of the magnetic stirrer to the stir bar.

A further embodiment of the stirring body is to form it such that it comprises two bar magnets and two vanes, the vanes having the form of a semi-ring in cross-section. What is disadvantageous with this embodiment is that, in this embodiment too, only a small force can be transmitted between the drive unit and the magnet, and thus no sufficient adhesive force of the magnets is given. Further, it is disadvantageous that, with this design of the stirring body, a relatively long time is required in order to achieve the desired heat distribution.

EP 1 186 653 A2 shows a bioreactor with a magnetic stirrer. The magnetic stirrer comprises a stirring body in a process chamber of the bioreactor and a drive unit outside the process chamber. The stirring body comprises several magnets which are arranged around magnets of the drive unit.

DE 11 2006 000 814 T5, too, shows a magnetic mixer in which magnets of the stirring body are arranged around magnets of the drive unit.

From DE 20 2004 013 715 U1 a drive device for a stirrer is known, in which again the magnets of the stirring body are arranged around magnets of a drive unit.

SUMMARY OF THE INVENTION

It is the object of the invention to specify a tissue processor comprising a magnetic stirrer with a stirring body as well as a stirring body for magnetic stirrers, with which a good stirring effect is achieved and in which a high force can be transmitted from a drive unit to the stirring body.

This object is solved by tissue processors and by stirring bodies having the features described herein.

The invention is characterized in that the stirring body has a first magnet the north pole of which faces the underside of the stirring body and thus the drive unit and the south pole of which faces away from the underside of the stirring body and thus from the drive unit, and in that the stirring body has a second magnet the south pole of which faces the underside of the stirring body and thus the drive unit and the north pole of which faces away from the underside of the stirring body and thus from the drive unit. As viewed from the direction of the drive unit, both magnets together appear as one big magnet having one north pole and one south pole. Hereby it is achieved that a high force can be transmitted from the drive unit via the magnetic field to the stirring body so that the stirring body can be operated at a high speed of rotation. As a result thereof, it can be achieved that the liquid is stirred well. Further, it is hereby achieved that due to the high force which can be transmitted from the drive unit to the stirring body, the stirring body does not have to be started-up slowly with a ramp, but can be immediately operated at full speed. Thus, also in the case of higher viscosity media the required magnetic adhesion is not lost. It is advantageous if the stirring body comprises at least three vanes. Hereby an even better stirring effect is achieved.

It is advantageous if the longitudinal axes of both magnets run on a common straight line and if the north pole and the south pole of both magnets are each separated from one another by a plane which includes the common straight line. It is particularly advantageous if the magnets have the shape of a cuboid. Hereby it is achieved that by means of the two magnets a symmetrical strong magnetic field is generated with respect to the axis of rotation of the stirring body so that the body of revolution can be uniformly driven with the aid of the drive unit and a high force can be transmitted from the drive unit to the stirring body. Hereby in turn a uniform strong stirring of the liquid is achieved.

The magnets are preferably made of neodymium N35. In this way, it is achieved that a strong magnetic field is generated by the two magnets and thus high forces can be transmitted from the drive unit to the stirring body. Alternatively, instead of neodymium N35 also neodymium-iron-boron compounds can be used.

It is advantageous if the two magnets are arranged opposite to one another with respect to the axis of rotation of the stirring body. In this way, it is achieved that a symmetrical magnetic field is generated with respect to the axis of rotation so that the forces exerted on the stirring body by the drive unit uniformly act on the stirring body, and the stirring body is uniformly driven.

In a preferred embodiment of the invention the stirring body comprises an even number of vanes, two vanes each being arranged opposite to one another with respect to the axis of rotation of the stirring body. By the symmetrical arrangement of the vanes and the symmetrical arrangement of the two magnets it is achieved that the stirring body is symmetrical with respect to the axis of rotation. By the symmetrical design of the stirring body it is guaranteed that it is uniformly driven by the drive unit and thus the liquid is uniformly stirred. In this way, a good stirring effect is achieved. In particular, a uniform turbulent flow is achieved hereby. The more turbulences are generated, in particular at the edge and/or in the corners of the process chamber, the better the heat energy can be transported away from the surface to the tissue samples. It is particularly advantageous if the stirring body comprises six vanes, wherein between two adjacent vanes or, respectively, between one of the magnets and one of the vanes adjacent thereto there is an angle of about 45° each time. In an alternative embodiment of the invention, the stirring body can also comprise four or eight vanes.

Further, it is advantageous if the vanes are identically formed. Hereby, a symmetrical design of the stirring body and a uniform stirring of the liquid are achieved. The vanes preferably have the shape of a blade. The vanes are preferably designed in a fluidically favorable manner so that the liquid to be stirred is optimally stirred. For this, the vanes preferably have the shape of a blade, in particular of a turbine blade.

Further it is advantageous if the stirring body has a hole, the center axis of which coincides with the axis of rotation. Hereby it is achieved that the stirring body can be placed over a pin which is arranged on a bottom of the process chamber, fixed to this bottom and formed complementarily to the hole so that a translation motion of the stirring body is prevented. Thus, it is prevented that the stirring body moves within the process chamber in an uncontrolled manner and could damage the process chamber and/or the tissue samples.

The stirring body preferably comprises an integrally formed basic body which comprises the vanes of the stirring body and two receiving elements, wherein one of the two magnets each is accommodated in the receiving elements. The two receiving elements each have an opening for insertion of the magnets. After insertion of the magnets, the openings of the receiving elements are preferably closed in a water-tight manner with the aid of one closing cap each. For this, the closing caps are welded thereto in particular by means of ultrasonic welding or laser welding. By integrally forming the basic body it is achieved that no joints occur and thus weakenings of the component are prevented, as a result whereof in turn the life of the component is increased. By receiving the magnets within the receiving elements and the water-tight closing of the openings of the receiving elements it is achieved that the magnets do not come into contact with the liquid, and thus any possibly damaging effects caused by the contact with the liquid, in particular with aggressive liquid, are prevented. The basic body is in particular made of polyoxymethylen (POM). POM is characterized on the one hand by a high chemical resistance to most liquids used, as well as by a high strength, hardness and stiffness. Thus, a long life of the component is achieved.

In a preferred embodiment of the invention the distance between the points of the receiving elements which are the furthest away from the axis of rotation and the axis of rotation is smaller than the distance between the points of the vanes which are the furthest away from the axis of rotation and the axis of rotation. Hereby it is achieved that the liquid optimally flows against the vanes so that it is achieved that the liquid is stirred well as desired.

BRIEF DESCRIPTION OF THE DRAWING VIEWS

Further features and advantages of the invention result from the following description which explains the invention in more detail in connection with the enclosed Figures with reference to embodiments.

DETAILED DESCRIPTION OF THE INVENTION

Figure 1:
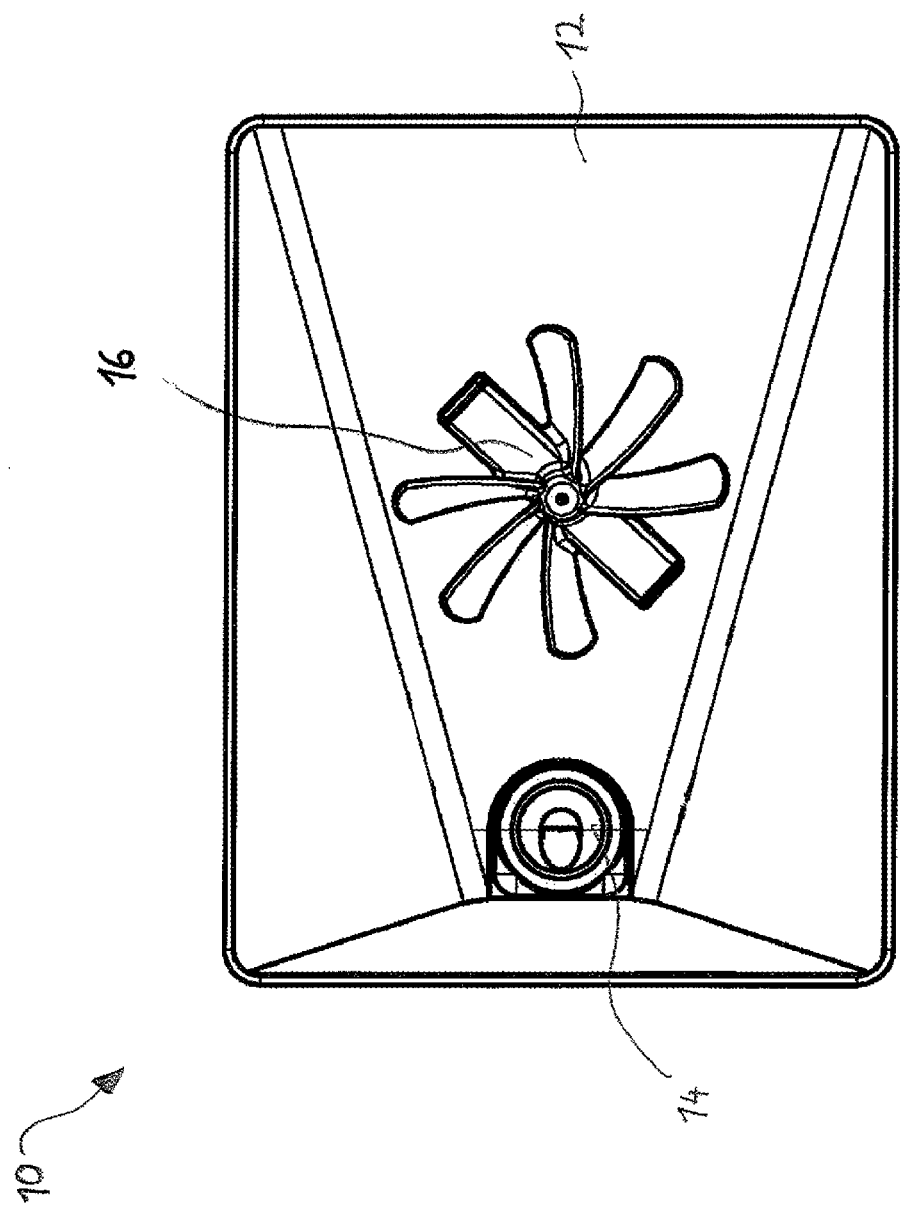
FIG. 1 shows a top view of a process chamber of a tissue processor.

In FIG. 1 a top view of a process chamber 10 of a non-illustrated tissue processor is shown. The process chamber 10 is also referred to as retort. It comprises a bottom in which an outlet 14 is arranged through which a liquid contained in the process chamber 10 can be drained off. The tissue processor serves for the treatment of tissue samples with liquids in order to prepare the tissue samples for a later microscopic examination. For this, at least one liquid and at least one tissue basket in which the tissue samples are arranged are placed in the process chamber 10. In order to guarantee a uniform treatment of the tissue samples with the liquid it is necessary that there are homogeneous properties, in particular a homogeneous heat distribution, all over the liquid. In order to achieve this, the process chamber 10 is formed as a vessel of a magnetic stirrer, and a stirring body 16 is arranged within the process chamber 10. When the stirring body 16 rotates, the liquid contained in the process chamber 10 is stirred so that inter alia a uniform heat distribution is achieved. In addition to a uniform heat distribution, in the case of liquids which are composed of several blending components, a stirring of the liquid results in a uniform distribution of the blending components. The stirring body 16 is also referred to as stirring bar, stir bar or flea.

Figure 2:
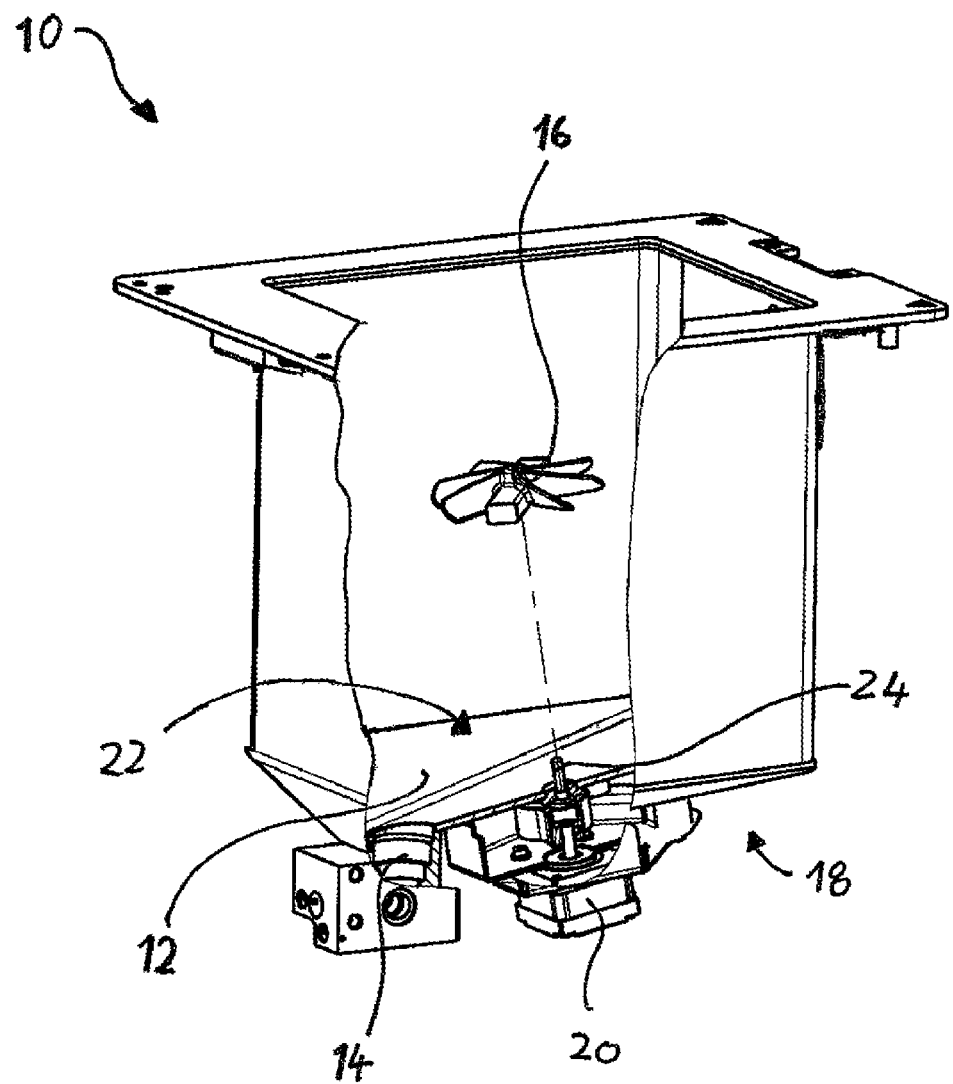
FIG. 2 shows a schematic side view in partial cross-section of the process chamber according to FIG. 1.

In FIG. 2, a schematic perspective illustration in partial cross-section of the process chamber 10 according to FIG. 1 is shown. Elements having the same structure or the same function are identified with identical reference signs.

At the side of the bottom 12 facing away from the process chamber 10, a drive unit 20 of the magnetic stirrer is arranged, with the aid of which the stirring body 16 can be set in rotation in a contact-free manner. The drive unit 20 is in particular an electric motor with the aid of which a permanent magnet is set in rotation. Due to the forces acting between the rotating magnet of the drive unit 20 and the magnet (described in more detail further below) of the stirring body 16, the stirring body 16 is likewise set in rotation when the magnet of the drive unit 20 rotates.

On the side 22 of the bottom 12 facing the stirring body 16, a pin 24 firmly connected to the bottom 12 is arranged, over which the stirring body 16 is placed so as to be rotatable. By the pin 24, a translation motion of the stirring body 16 is prevented so that this pin cannot freely move in the process chamber 10, and thus damages to the process chamber 10 and/or damages to the tissue samples contained in the process chamber 10 are avoided. The stirring body 16 is placed over the pin 24 such that it can merely perform a rotation about an axis of rotation A. The pin 24 is not driven and in particular does not rotate.

Figure 3:
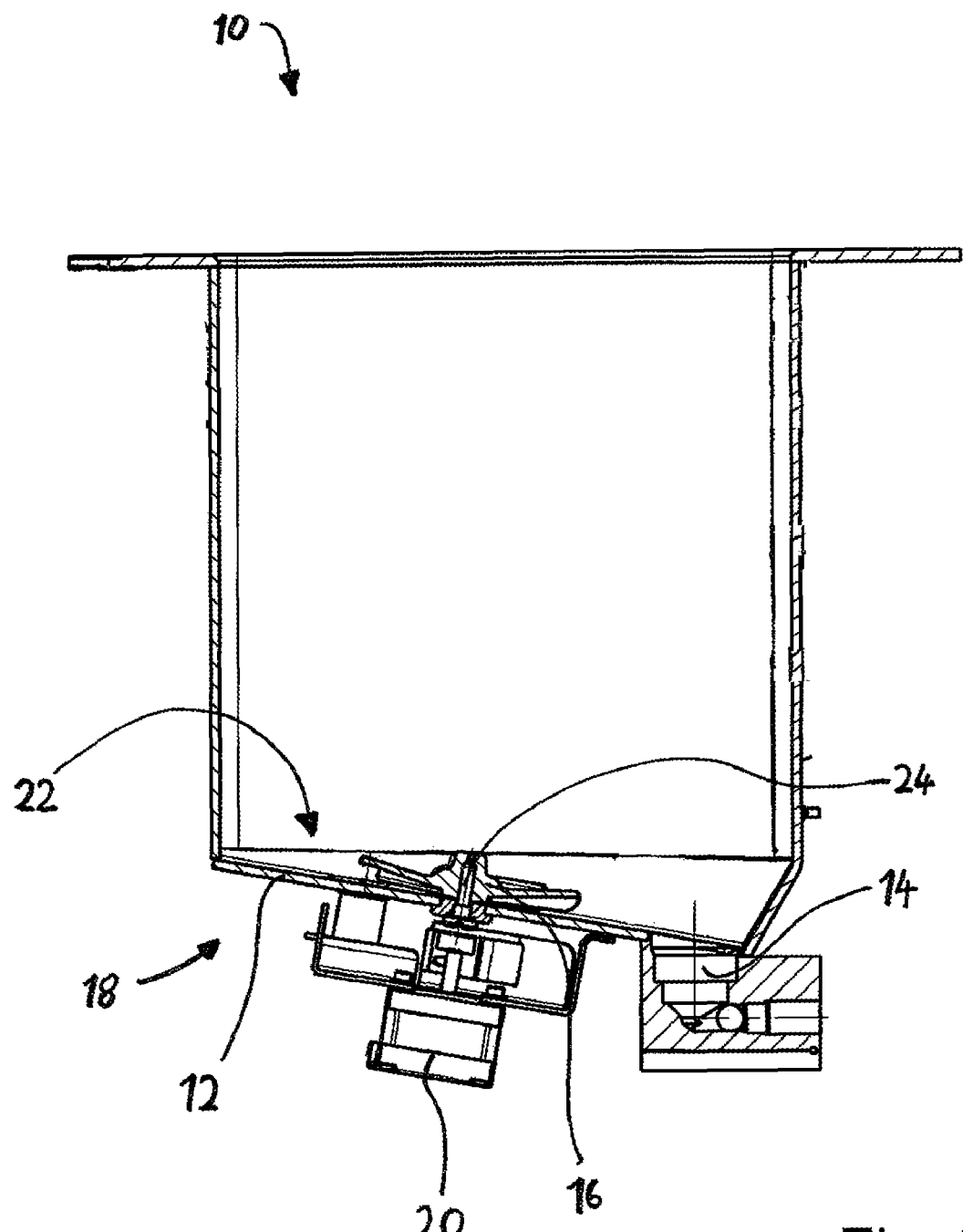
FIG. 3 shows an illustration in cross-section of the process chamber according to FIGS. 1 and 2.

In FIG. 3, an illustration in cross-section of the process chamber 10 according to FIGS. 1 and 2 is shown. The stirring body 16 is placed over the pin 24.

Figure 4:
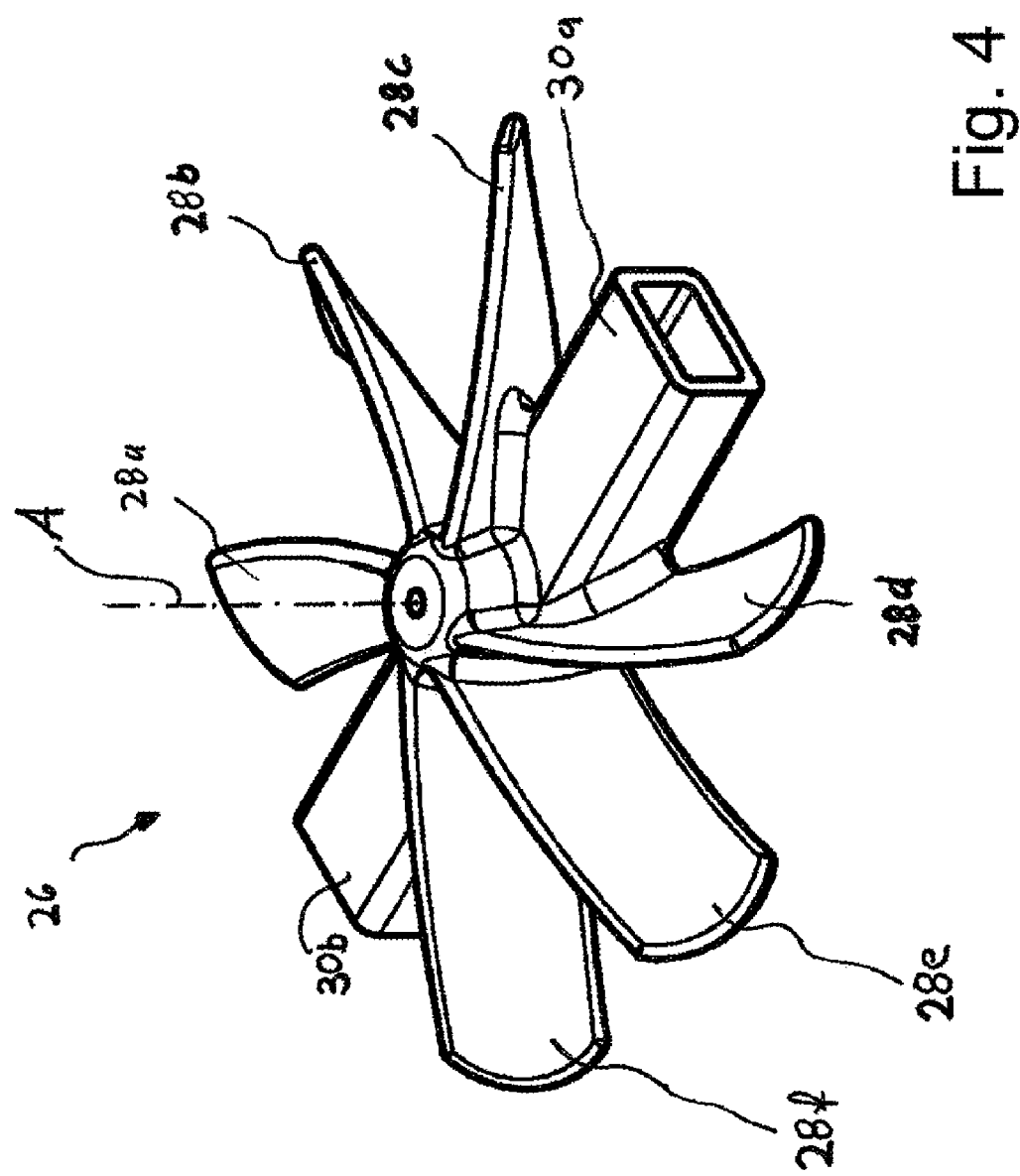
FIG. 4 shows a schematic perspective illustration of a basic body of the stirring body.

In FIG. 4, a schematic perspective illustration of a basic body 26 of the stirring body 16 is shown. The basic body 26 comprises six vanes 28a to 28f and two receiving elements 30a, 30b. The basic body 26 is integrally formed and preferably made of polyoxymethylene (POM), in particular POM-C natural. Hereby a high strength, hardness and stiffness of the basic body 26 is achieved. Further, by making the basic body 26 of POM it is achieved that it is chemically inert with respect to the common liquid used for treating the tissue samples so that the basic body 26 is not damaged by the liquid.

In an alternative embodiment of the invention, the basic body 26 can also be formed of several parts welded together. Further, the basic body 26 can also be made of other materials and/or comprise more or less than six vanes 28a to 28f.

The basic body 26 is formed symmetrically with respect to the axis of rotation A so that, upon a rotation about this rotation axis A, it uniformly stirs the liquid, as a result whereof the desired uniform distribution of the liquid and the desired uniform heat distribution is quickly achieved in an easy manner. For this, the six vanes 28a to 28f are in particular identically formed. The receiving elements 38a, 30b are likewise identically formed.

Figure 5:
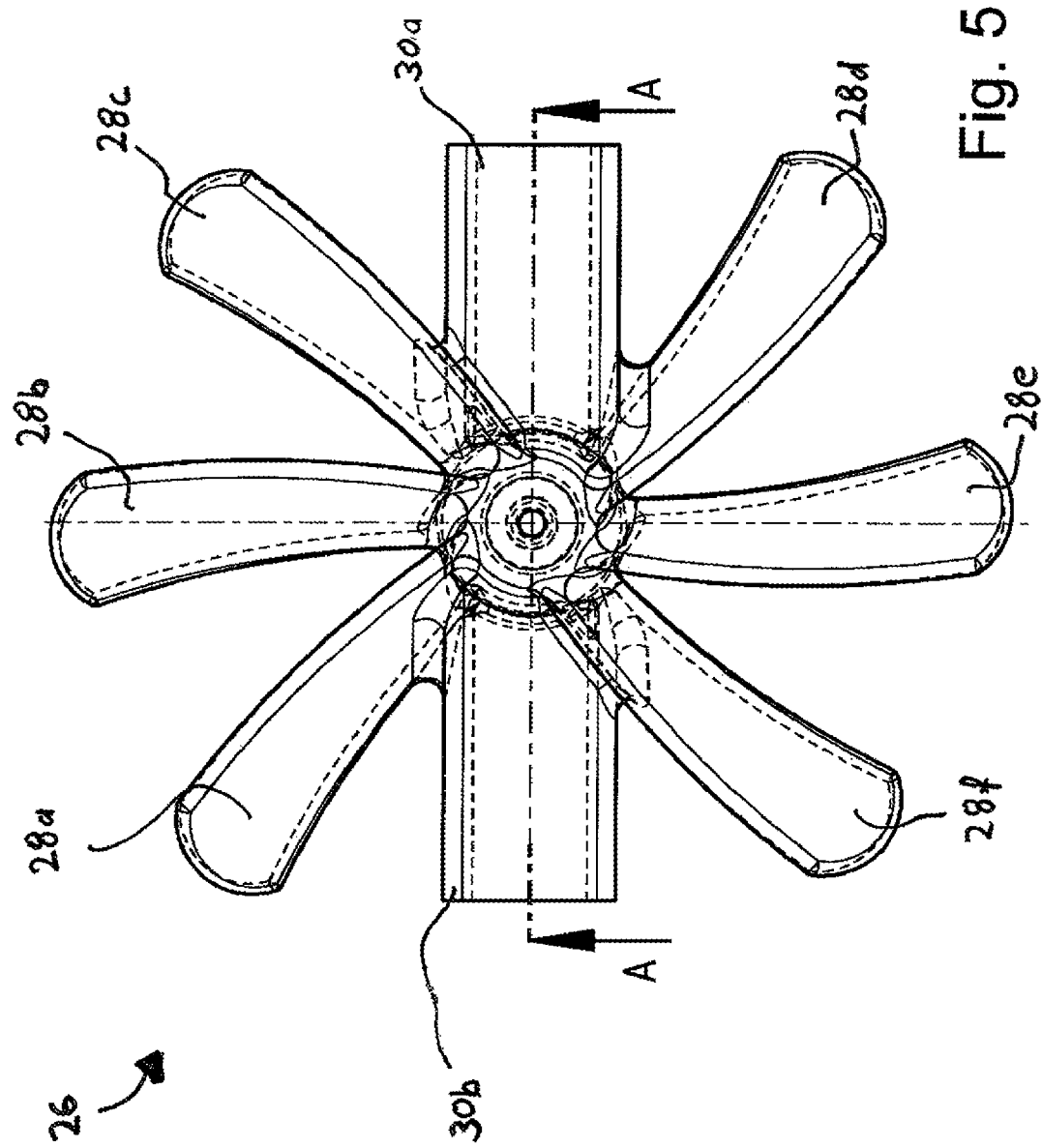
FIG. 5 shows a top view of the basic body of the stirring body according to FIG. 4.

In FIG. 5, a top view of the basic body 26 according to FIG. 4 is shown. The basic body 26 has a diameter in the range between 70 to 80 mm, in particular of 75 mm. This maximum diameter is the distance between the point of a vane 28a to 28f which is furthest away from the axis of rotation A and the point of the vane 28a to 28f opposite to the vane 28a to 28f which point is furthest away from the axis of rotation A. The distance between the points which are furthest away from the axis of rotation A and the axis of rotation A is smaller than the distance between the points of the receiving elements 30a, 30b which are furthest away from the axis of rotation A and the axis of rotation A. Hereby it is achieved that the liquid optimally flows against the vanes 28a to 28f when the stirring body 16 rotates so that the liquid is well-stirred by the vanes 28a to 28f.

Figure 6:
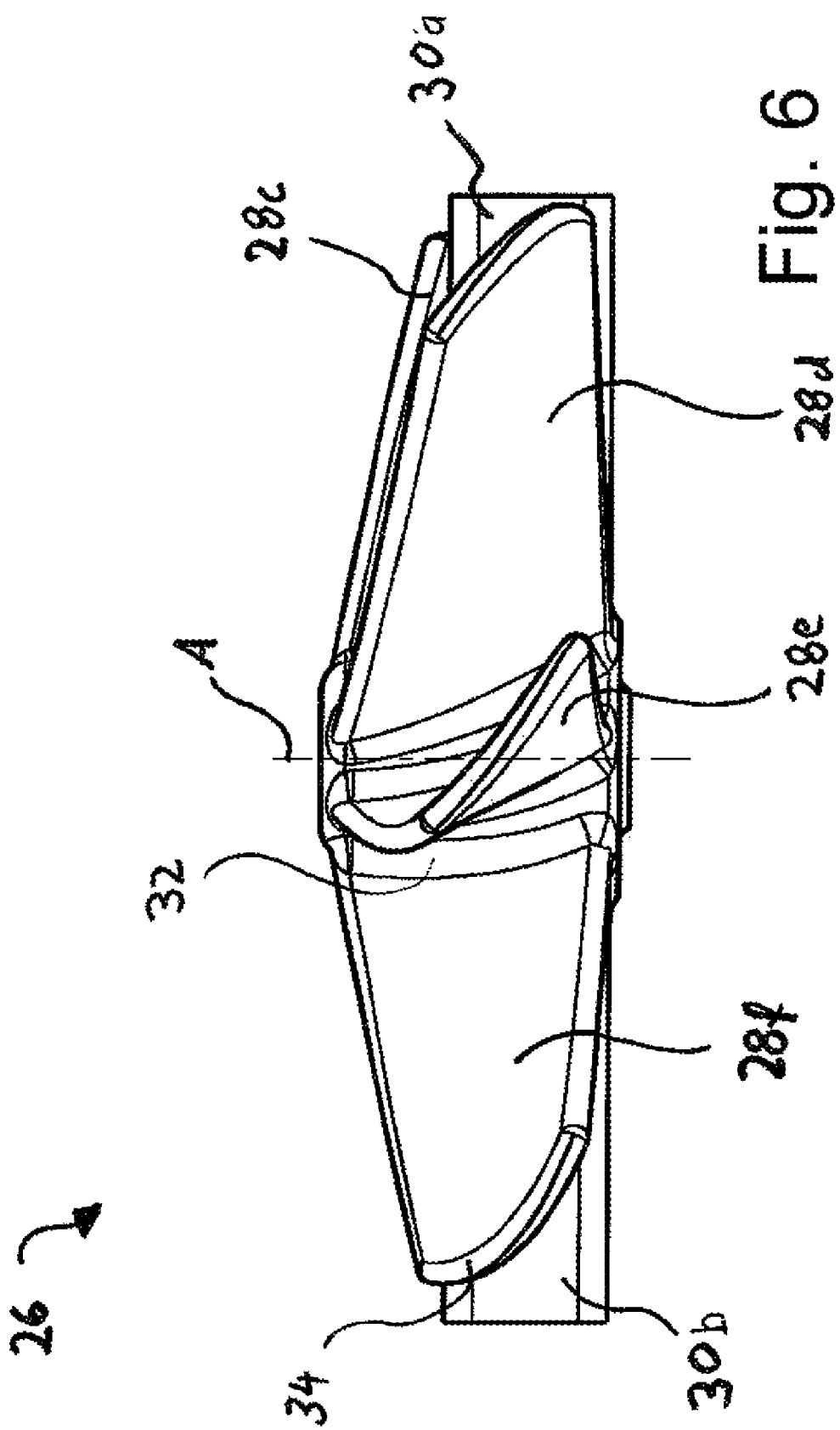
FIG. 6 shows a side view of the basic body of the stirring body according to FIGS. 4 and 5.
Figure 7:
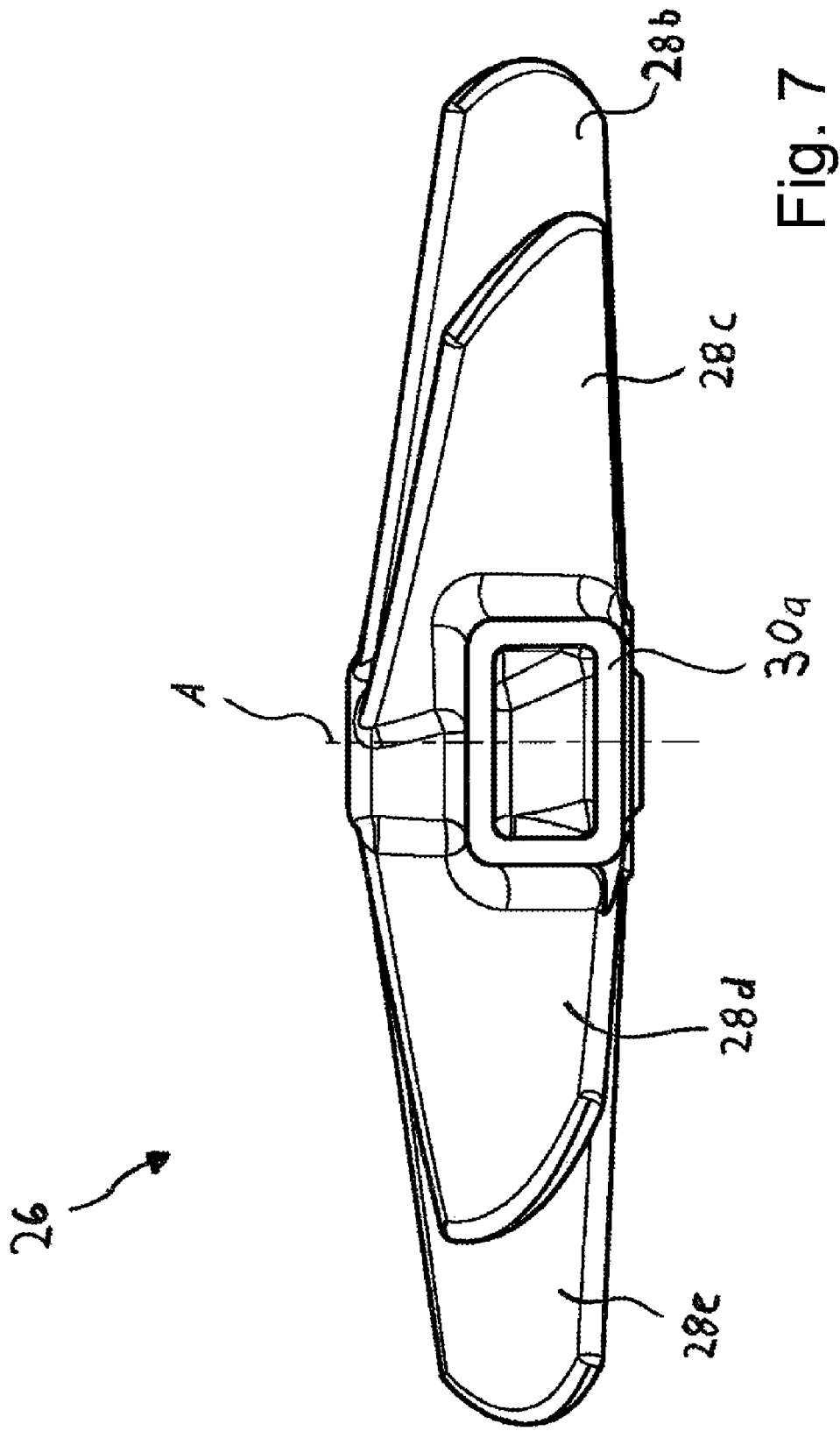
FIG. 7 shows a further side view of the basic body of the stirring body according to FIGS. 4 to 6.

In FIG. 6, a first side view of the basic body 26 according to FIGS. 4 and 5 is shown. In FIG. 7, a second side view of the basic body 26 according to FIGS. 4 to 6 is shown, wherein the basic body 26 in FIG. 7 is rotated by 90° about the axis of rotation A compared to FIG. 6. From FIGS. 6 and 7, the shape of the vanes 28a to 28f can easily be taken. The vanes have a fluidically favorable design so that a stirring as good as possible of the liquid to be stirred is achieved. For this, the vanes have the shape of a blade. The shape of the vanes is in particular similar to the shape of turbine blades.

The vanes 28a to 28f have a slightly curved shape so that the liquid to be stirred is carried away upwards with the arrangement of the basic body 26 shown in FIGS. 6 and 7. Further, the vanes 28a to 28f are each formed slightly twisted so that the end 32 of the vane 28a to 28f facing the axis of rotation A runs almost parallel to the axis of rotation A, whereas the end 34 of the respective vane 28a to 28f facing away from the axis of rotation A has an angle of less than 90°, in particular an angle between 30° and 60°, with respect to the axis of rotation A.

Figure 8:
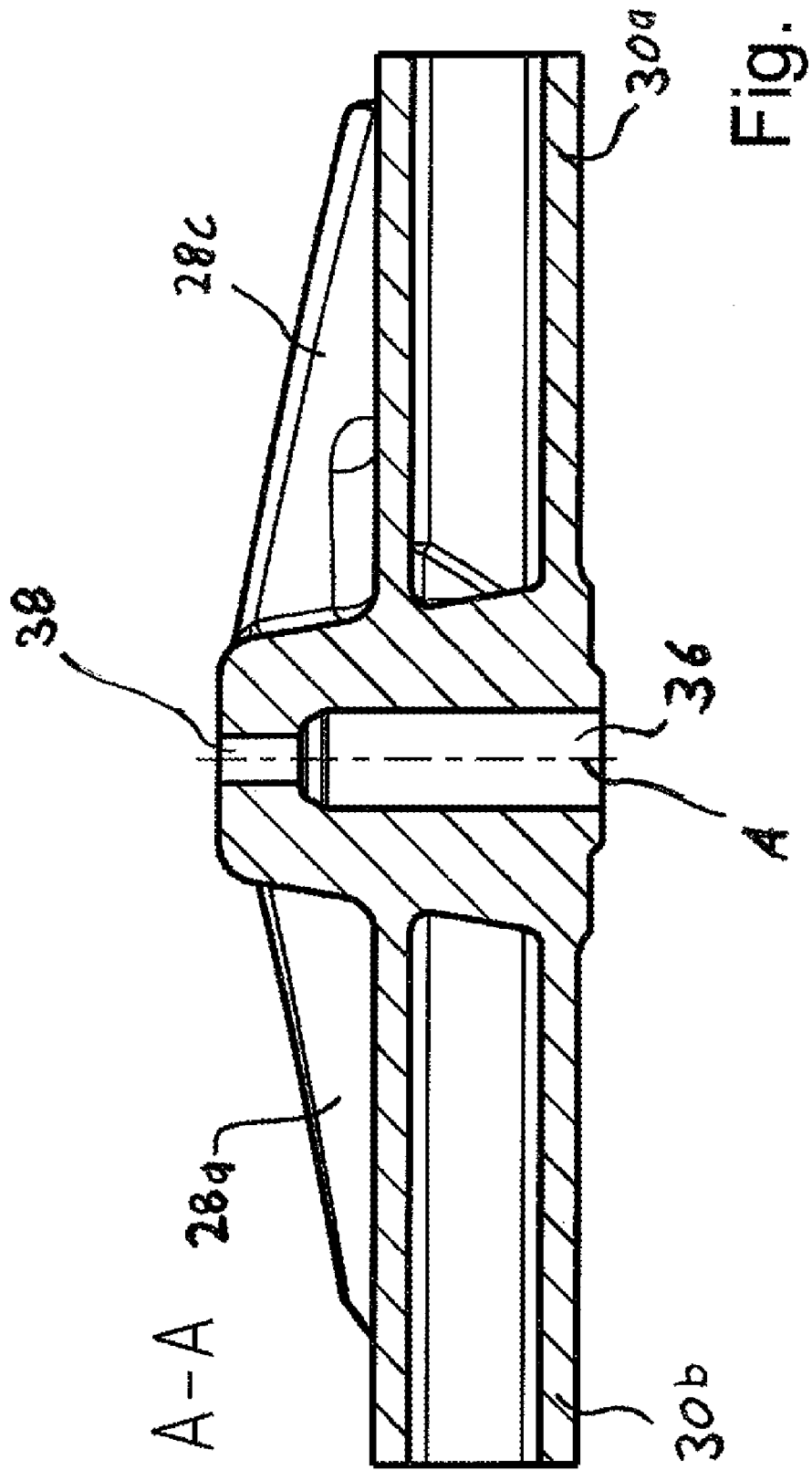
FIG. 8 shows an illustration in cross-section of the basic body along the line A-A of FIG. 5.

In FIG. 8, an illustration in cross-section of the basic body 26 according to FIGS. 4 to 7 along the line A-A of FIG. 5 is shown. The basic body 26 has a recess 36 formed complementarily to the pin 24, by which recess the stirring body 16 can be placed over the pin 24. The recess 36 is in particular arranged such that its longitudinal axis coincides with the axis of rotation A. Further, the basic body 26 comprises a further recess 38 which adjoins the recess 36 and the center axis of which lies on a straight line with the center axis of the recess 36. What is achieved by this recess 38 is that the basic body 26 has a continuous recess as a result of the two recesses 36, 38 so that, unlike in the case of a non-continuous recess, no liquid can collect within the recess and thus a floating of the stirring body 16 and thus a loosening of the stirring body 16 from the pin 24 is prevented.

Figure 9:
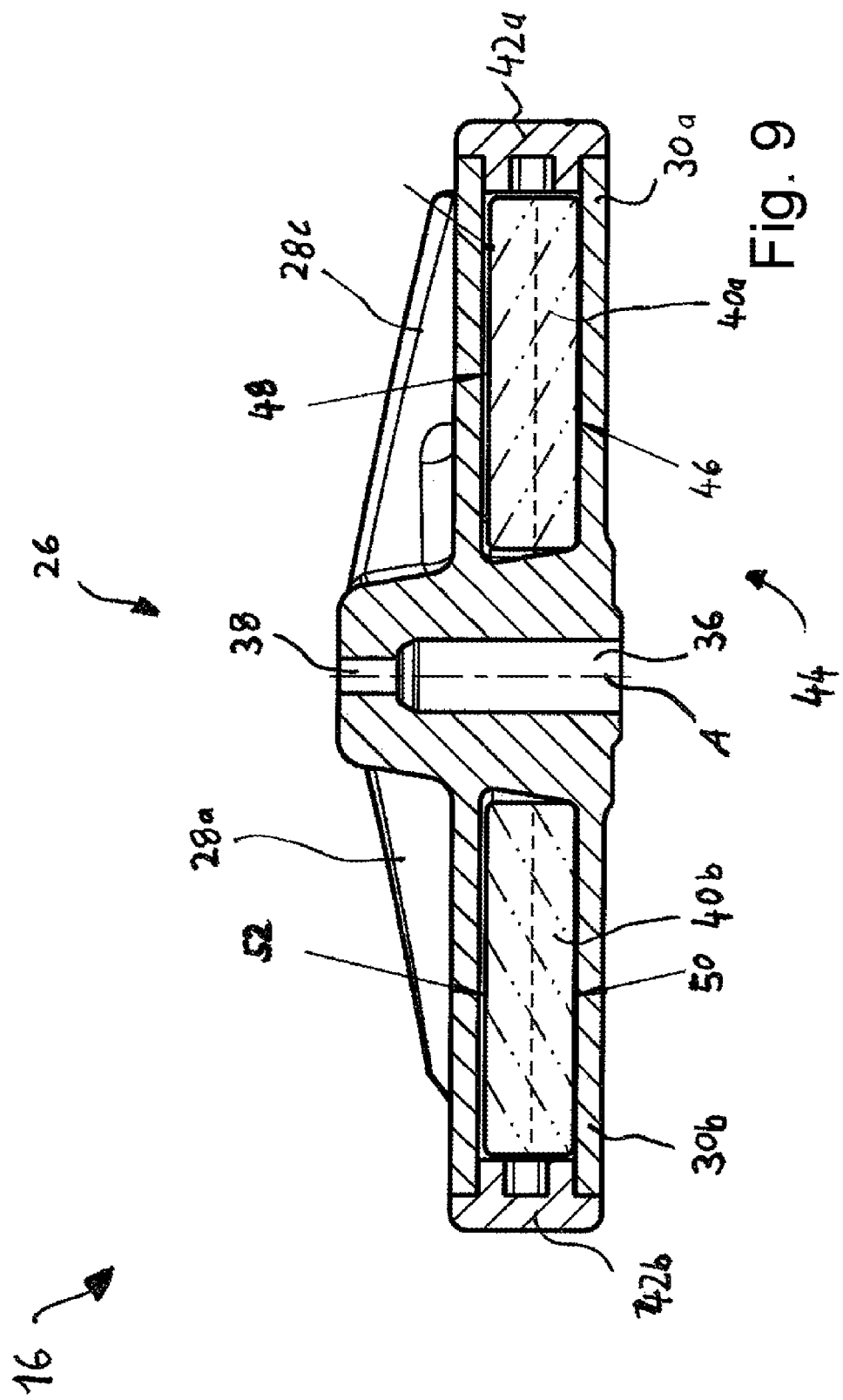
FIG. 9 shows an illustration in cross-section of the stirring body according to FIGS. 4 to 8, with magnets received therein and closing caps fitted thereon.

In FIG. 9, an illustration in cross-section of the stirring body 16 is shown. In addition to the basic body 26, the stirring body 16 comprises two magnets 40a, 40b and two closing caps 42a, 42b. The magnets 40a, 40b are received in the two receiving elements 30a, 30b. During assembly, the openings through which the magnets 40a, 40b are fed to the receiving elements 30a, 30b are closed in a watertight manner with the aid of two closing caps 42a, 42b, after the magnets 40a, 40b have been inserted into the receiving elements 30a, 30b. What is achieved by means of the watertight closing is that the magnets 40a, 40b do not come into contact with the liquid so that damages to the magnets 40a, 40b by possible reactions with the liquid are avoided. The closing caps 42a, 42b are in particular welded thereto. In an alternative embodiment of the invention, the closing caps can also only be clipped on so that these can easily be removed again non-destructively, for example in order to replace the magnets 40a, 40b.

The magnets 40a, 40b are in particular dimensioned such that they are received in the receiving elements 30a, 30b as positive as possible so that a slipping of the magnets 40a, 40b within the receiving elements 30a, 30b is avoided or at least reduced. The first magnet 40a is arranged such that its north pole 46 faces the underside of the stirring body 16 and thus the drive unit 20. Its south pole 48, in contrast, faces away from the drive unit 20. On the other hand, the second magnet 40b is arranged such that a south pole 50 faces the underside 44 and thus the drive unit 20, whereas its north pole 52 faces away from the drive unit 20. By this arrangement of the magnets 40a, 40b it is achieved that the magnetic field created thereby, as viewed from the drive unit 20, appears as the magnetic field of one big continuous magnet having a north pole arranged instead of the first magnet 40a and a south pole arranged instead of the second magnet 40b. Due to the strong magnetic field created in this way, high forces can be transmitted by the drive unit 20 onto the stirring body 16 so that this one can be operated at a high rotational speed and this high rotational speed can also be used straight from the beginning, even with media having a higher viscosity and no slow start-up is necessary.

The magnets 40a, 40b in particular have the shape of a cuboid. Hereby, the above-described effect is increased. Further, the magnets 40a, 40b are made of neodymium N35 which has very good magnetic properties so that strong forces can be transmitted from the drive unit 20 via the magnetic field onto the stirring body 16. In an alternative embodiment of the invention, the magnets 40a, 40b can also have a shape different from a cuboid and/or be made of a different material. Further, more than two magnets 40a, 40b can alternatively be used, in particular four magnets can be provided. The magnets are in particular arranged such that two adjacent magnets each have the same angle with respect to one another. In this way, it is achieved that the stirring body 16 is uniformly set in rotation so that a uniform stirring effect is achieved.

Figure 10:
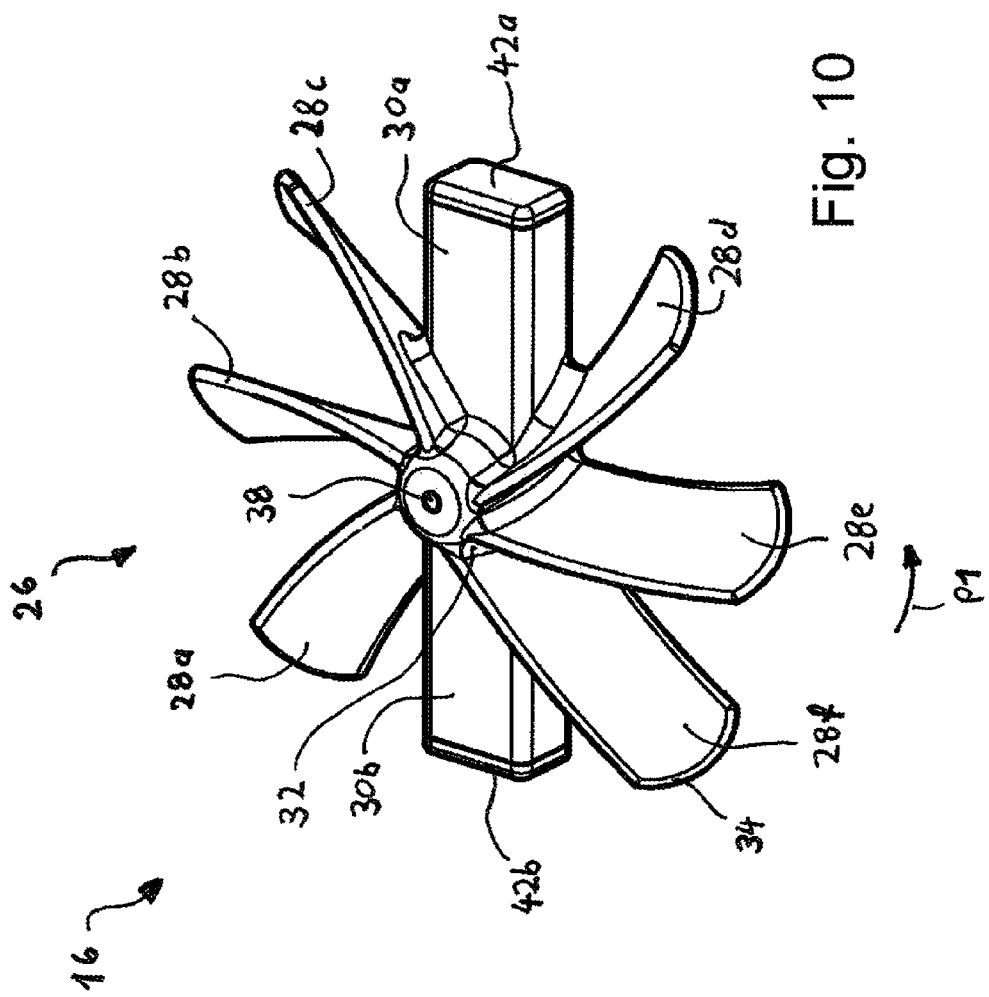
FIG. 10 shows a schematic perspective illustration of the stirring body according to FIG. 9.

In FIG. 10 a schematic perspective illustration of the stirring body 16 according to FIG. 9 is shown. The direction of rotation of the stirring body 16 is indicated by the arrow P1.

Figure 11:
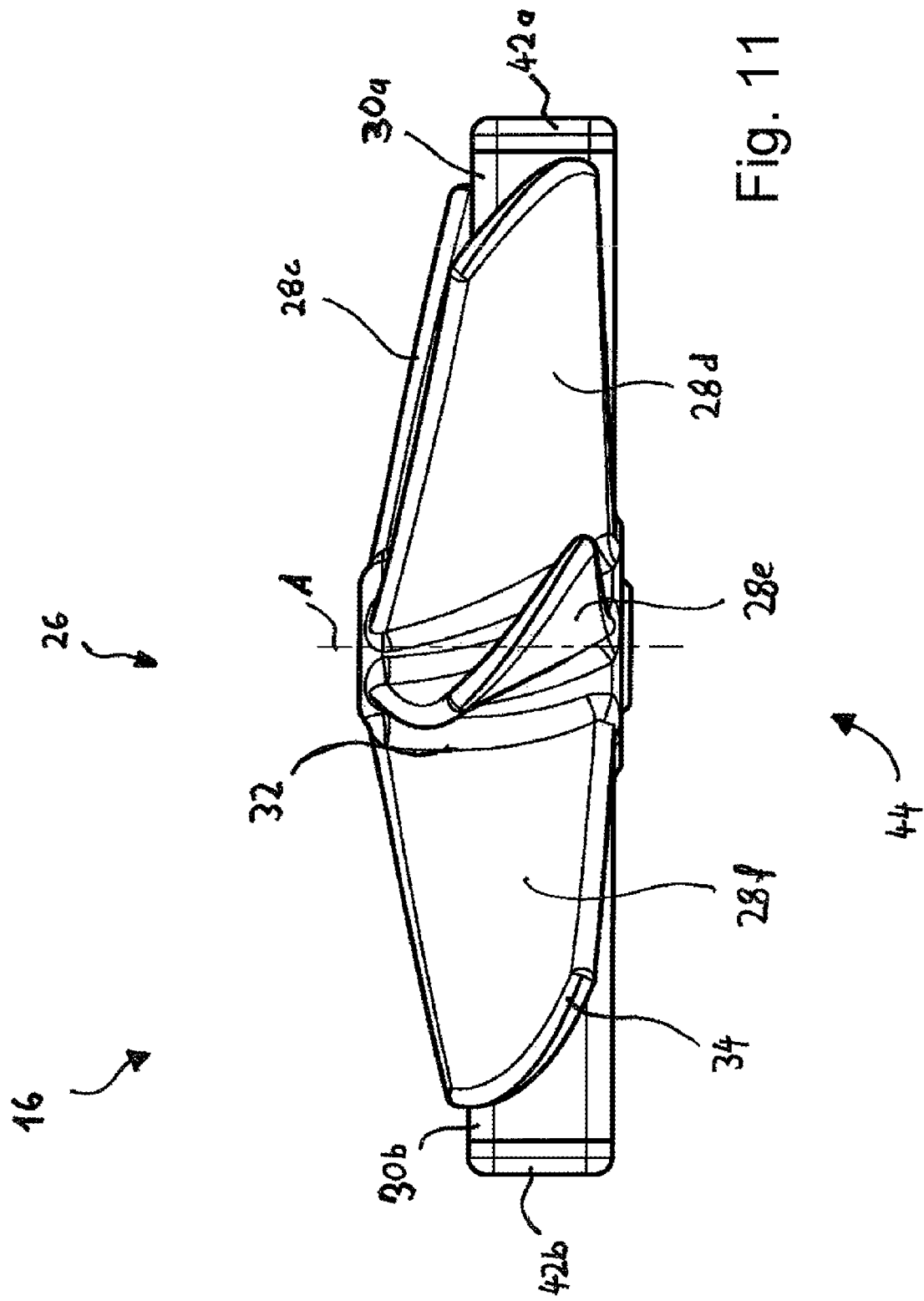
FIG. 11 shows a side view of the stirring body according to FIGS. 9 and 10.

In FIG. 11, a side view of the stirring body 16 according to FIGS. 9 and 10 is illustrated. The receiving elements 30a, 30b are closed by the closing caps 42a, 42b.

The above-described stirring body 16 can also be used in magnetic stirrers outside of tissue processors. Further, the stirring body 16 can be designed such that its vanes 28a to 28f are not identically shaped. In a further alternative embodiment of the invention, the stirring body 16 can also have no recess 36, 38 and thus it can freely move in the vessel of the magnetic stirrer.

LIST OF REFERENCE SIGNS 10 process chamber
12 bottom
14 outlet
16 stirring body
18 side
20 drive unit
22 side
24 pin
26 basic body
28a to 28f vanes
30a, 30b receiving element
32, 34 vane end
36, 38 recess
40a, 40b magnet
42a, 42b closing cap
44 underside
46, 52 north pole
48, 50 south pole
A axis of rotation
P1 direction of rotation

What is claimed is:

1. A tissue processor for treating tissue samples, comprising:
    a process chamber configured to contain at least one liquid and to receive tissue samples for treating the tissue samples with the at least one liquid, the process chamber having a bottom, wherein the process chamber forms a vessel of a magnetic stirrer;
    a drive unit arranged on a side of the bottom facing away from the process chamber; and
    a stirring body arranged within the process chamber for stirring the liquid in the process chamber, wherein the stirring body is caused to rotate in a contact-free manner by the drive unit;
    a pin located in the bottom of the process chamber, wherein the stirring body further includes a hole having a center axis coinciding with the axis of rotation of the stirring body, the pin being arranged complimentary to the hole so that the stirring body is placed over the pin and at least a portion of the pin is received within the hole;
    wherein the stirring body includes at least one vane for stirring the liquid when the stirring body is rotated,
    wherein the stirring body further includes a first magnet having a north pole facing an underside of the stirring body and thus the drive unit, and a south pole facing away from the underside of the stirring body and thus away from the drive unit; and
    wherein the stirring body further includes at least a second magnet having a south pole facing the underside of the stirring body and thus the drive unit and a north pole facing away from the underside of the stirring body and thus away from the drive unit.

2. The tissue processor according to claim 1, wherein the first magnet and second magnet each have the shape of a cuboid.

3. The tissue processor according to claim 1, wherein the first magnet and the second magnet are each made of neodymium N35.

4. The tissue processor according to claim 1, wherein the first magnet and the second magnet are arranged opposite to one another with respect to an axis of rotation of the stirring body.

5. The tissue processor according to claim 1, wherein the at least one vane of the stirring body is an even number of vanes, and each of the vanes is arranged opposite to one other of the vanes with respect to an axis of rotation of the stirring body.

6. The tissue processor according to claim 5, wherein the even number of vanes is six vanes.

7. The tissue processor according to claim 5, wherein the stirring body has an integrally formed basic body, the basic body comprising the vanes of the stirring body, a first receiving element having an opening for receiving the first magnet, and a second receiving element having another opening for receiving the second magnet.

8. The tissue processor according to claim 7, wherein a combined length of the receiving elements is less than the diameter of a circle about the axis of rotation defined by points on the vanes furthest away from the axis of rotation.

9. The tissue processor according to claim 1, wherein the at least one vane has the shape of a turbine blade.

10. A tissue processor for treating tissue samples, comprising:
    a process chamber configured to contain at least one liquid and to receive tissue samples for treating the tissue samples with the at least one liquid, the process chamber having a bottom, wherein the process chamber forms a vessel of a magnetic stirrer;
    a drive unit arranged on a side of the bottom facing away from the process chamber; and
    a stirring body arranged within the process chamber for stirring the liquid in the process chamber, wherein the stirring body is caused to rotate in a contact-free manner by the drive unit;
    wherein the stirring body includes at least one vane for stirring the liquid when the stirring body is rotated,
    wherein the stirring body further includes a first magnet having a north pole facing an underside of the stirring body and thus the drive unit, and a south pole facing away from the underside of the stirring body and thus away from the drive unit;
    wherein the stirring body further includes at least a second magnet having a south pole facing the underside of the stirring body and thus the drive unit and a north pole facing away from the underside of the stirring body and thus away from the drive unit; and
    wherein the first magnet and the second magnet each have a respective longitudinal axis, the longitudinal axes of the first and second magnets are aligned to extend along a common straight line, and in each of the first and second magnets the north pole thereof is separated from the south pole thereof by a plane which includes the common straight line.

* * * * *